(12) United States Patent
Schonert et al.

(10) Patent No.: US 7,771,734 B2
(45) Date of Patent: Aug. 10, 2010

(54) PROCESS TO COLOR AND PERMANENTLY RESTRUCTURE HAIR

(75) Inventors: Dieter Schonert, Reinheim-Georgenhausen (DE); Anette Schmidt-Hoerr, Gross-Bieberau (DE)

(73) Assignee: Wella AG, Darmstadt (DE)

( * ) Notice: Subject to any disclaimer, the term of this patent is extended or adjusted under 35 U.S.C. 154(b) by 523 days.

(21) Appl. No.: 11/260,604

(22) Filed: Oct. 27, 2005

(65) Prior Publication Data

US 2006/0096042 A1 May 11, 2006

(30) Foreign Application Priority Data

Nov. 5, 2004 (DE) .................. 10 2004 054 055

(51) Int. Cl.
*A61K 8/64* (2006.01)
*A61K 8/00* (2006.01)
*A61K 8/18* (2006.01)
*D06M 11/26* (2006.01)
*A61Q 5/10* (2006.01)
*A45D 7/04* (2006.01)

(52) U.S. Cl. .................. 424/401; 132/202; 132/204; 132/205; 132/206; 132/208; 8/405; 8/406; 8/407; 8/408; 8/409; 424/70

(58) Field of Classification Search ............. 8/405–412, 8/423; 132/202, 204, 205, 206, 208, 210; 424/70.51

See application file for complete search history.

(56) References Cited

U.S. PATENT DOCUMENTS

| 2,869,559 | A | * | 1/1959 | Moore ................. 132/203 |
| 4,395,262 | A | * | 7/1983 | Konrad et al. ........... 8/410 |
| 6,173,717 | B1 | * | 1/2001 | Schonert et al. ......... 132/202 |
| 6,945,254 | B2 | * | 9/2005 | Schonert et al. ......... 132/202 |

FOREIGN PATENT DOCUMENTS

| DE | 1129261 | 5/1962 |
| EP | 0352375 | 1/1990 |
| GB | 876663 | 6/1960 |

OTHER PUBLICATIONS

John A. Wenninger, et al; "International Cosmetic Ingredient Dictionary and Handbook", 8th Ed; 2000; pp. 1141-1143.
R. Heilingoetter, "Permanent Waves and Hair Coloring in One Work Step", Kosmetik-Parfuem-Drogen Rundschau [Cosmetics Industry Journal] 3/4 (1965) pp. 35 & 36.
Clarence R Robins: "Chemical and Physical Behavior of Human Hair", 3-D Edition, Springer Verlag, 1994.

* cited by examiner

*Primary Examiner*—Johann R Richter
*Assistant Examiner*—Luke E Karpinski
(74) *Attorney, Agent, or Firm*—Michael J. Striker

(57) ABSTRACT

Process to simultaneously color and permanently restructure hair, wherein
(a) an oxidative hair colorant is applied to the hair based on at least one developer substance and least one coupler substance,
(b) the oxidative hair colorant is left on for 5 to 60 minutes,
(c) the oxidative hair colorant is rinsed out of the hair,
(d) an acidic intermediate treatment agent with a pH of from 2 to 6 is applied to the hair,
(e) after an action period of from 1 to 10 minutes, the intermediate treatment agent is rinsed out, if necessary, and the hair is then rolled up onto curlers,
(f) a keratin-reducing permanent restructuring agent is applied to the hair,
(g) after an action period of from 1 to 30 minutes, the keratin-reducing agent is rinsed out, if necessary,
(h) the hair is fixed with an oxidative material,
(i) after an action period of from 3 to 15 minutes, the hair is rinsed with water, if necessary and then treated with an acidic rinse.

The process is intended to enable better, faster, and gentler coloring of human hair, particularly natural hair, than was previously possible, as well as to maintain the color intensity of colored hair or to refresh (renew) it, and to improve the hair shine while simultaneously restructuring the hair.

13 Claims, No Drawings

PROCESS TO COLOR AND PERMANENTLY RESTRUCTURE HAIR

CROSS-REFERENCE TO RELATED APPLICATIONS

This application claims priority under 35 U.S.C. 119(a)-(d) to German Patent Application 10 2004 052055.1, filed on Nov. 5, 2004.

BACKGROUND OF THE INVENTION

1. Field of the Invention

The object of the present invention is a process to color and permanently restructure hair, in which one process is carried out after the other on the same day—preferably one right after the other. It is particularly suitable for natural hair and colored hair.

In Step 1, the hair is colored using oxidation. After an action period of from 5 to 60 min (preferably 10 to 30 min), the colorant is rinsed from the hair. In Step 2, the hair is given an intermediate acidic treatment. After the action period has elapsed, the intermediate treatment agent is rinsed out (or can be left in the hair), followed by Step 3, the permanent wave process, which is carried out with the aid of a keratin-reducing agent. After an action period of 1 to 30 min, the keratin-reducing agent is rinsed out as necessary. In Step 4, the sulfuric bridges are closed after the restructuring via an agent containing peroxide. Step 5 represents the final treatment via an acidic agent (anionic/cationic).

2. Description of Related Art

The classic technique for implementing permanent hair restructuring involves a first stage in which the disulfide bonds of the hair keratin are opened with the aid of an agent containing a reducing material (restructuring agent); the hair is then changed to the desired form, and, subsequently, the disulfide bonds are linked back together again using an oxidative material (fixing agent). Sulfites, mercaptoacetic acid, thiolactic acid, 3-mercaptopropionic acid, mercaptocarboxylic acid ester, and cysteine are used in particular as reducing materials. These agents are either acidic (sulfite, bisulfite, and mercaptocarboxylic acid ester) or alkaline (alkali and ammonium salts of mercaptocarboxylic acids). In the case of alkaline restructuring agents, the required alkalinity is obtained primarily by adding ammonia, organic amines, ammonium or alkali carbonate, and ammonium or alkali hydrogen carbonates. Liquids containing hydrogen peroxide or bromate are particularly used as fixing agents.

The permanent restructuring of human hair occurs, in general, by first separating the hair (which is washed and towel-dried) into multiple sections and then rolling these sections onto curlers. After the rolling process is finished, the curlers are thoroughly wetted down using the required quantity of the permanent restructuring agent. The curlers used for permanent waves have a diameter of about 5 to 13 millimeters (0.17 to 0.44 in), while the curlers used for straightening must have a diameter greater than 13 millimeters (0.44 in).

The amount of time the restructuring agent stays on the hair with a permanent wave is about 1 to 30 minutes depending on hair quality and the desired level of change. This action time can be shortened by adding heat via the use of a heat radiator or a hood dryer.

After the required action period for the restructuring agent has elapsed, the hair is rinsed with water and treated with a fixing agent, for example, an aqueous solution of hydrogen peroxide or potassium bromate. The action period of the fixing agent in this case is normally about 1 to 20 minutes. The curlers are then removed; if necessary, the hair is retreated with the fixing agent for a few minutes, and then rinsed thoroughly with water; the hair is styled and then dried.

Oftentimes, however, it is not just a restructuring of the hair that is desired, but also coloring or tinting. Up to now, the request for a color and wave treatment could only be carried out with a break in between of at least one week in order to obtain sufficient structure of the hair.

For this reason, there have already been many attempts made to enable the restructuring and coloring of hair in one work step. Thus, for example, a process is known from DE-AS 1 129 261 as well as GB-PS 876 663 that enables simultaneous permanent waving and coloring of hair, including white and gray hair. This process is based on a restructuring agent that consists of an aqueous solution of a keratin-reducing agent and a suitable basic dye. The dyes used, for example, crystal violet, methylene blue, fuchsin, or malachite green, are present in the form of stable leuco compounds and are not converted into the actual dye until the subsequent oxidative fixation.

The overview article entitled "Permanent waves and hair coloring in one work step" by R. Heilingötter, Kosmetik-Parfüm-Drogen Rundschau [Cosmetics industry journal] 3/4 (1965), Pages 35 and 36, presents the option of simultaneous tinting and restructuring of hair by adding oxidative dyes (in the form of their precursors) to an alkaline thioglycolate solution. Finally, EP-B 0 352 375 contains a process for permanently restructuring and simultaneously coloring hair in which the hair is first treated for 8 to 20 minutes with a first agent contained as keratin-reducing agents, 0.1 to 6 wt % thioglycolate, and 3 to 10 wt % cysteine as well as, as oxidative dyes, 0.01 to 4 wt % para- and/or orthophenylendiamine, 0.01 to 1 wt % resorcinol, as well as 0.01 to 1 wt % antioxidants, 0.01 to 1 wt % heavy-metal chelating agents, 0.01 to 1 wt % surfactant and alkalizing agents to create a pH of from 9.0 to 9.5; a second agent with 3 to 8 wt % hydrogen peroxide is then applied without any prior rinsing.

All of the previously described procedures for permanent restructuring and simultaneous coloring or tinting of hair, however, have the disadvantage that the targeted results are not always satisfactory.

Conventional permanent wave procedures cause, particularly with colored hair, a strong loss of color. Natural hair that has been permanently waved, loses a noticeable amount of shine and is sometimes lightened by the treatment. Hair becomes dull and listless.

BRIEF SUMMARY OF THE INVENTION

Thus, the object of the present invention is to provide a process to color and maintain the color intensity of human hair, particularly natural hair, that is better, quicker, and gentler than was previously available, and to improve shine with the simultaneous restructuring of hair.

The advantages of the present process are found in the improved durability of the color and in an improved durability of the restructuring in comparison to hair restructuring and coloring with a break of a least one week between processes. Furthermore, the shine of the hair is visibly increased. The entire treatment sequence is easier on the hair in comparison to the normal treatment sequence of permanent hair restructuring. The efficient implementation on the same day also provides the customer an advantage in comfort and convenience in comparison to conventional methods.

DETAILED DESCRIPTION OF THE INVENTION

With the process according to the present invention, a colorant (component A) is first applied to—preferably dry—hair, and then washed out after an action period of from 5 to 60 minutes, or preferably 10 to 45 minutes. Subsequently, the hair is neutralized with an acidic intermediate treatment agent with a pH of from 2 to 6, or preferably 2 to 3 (component B), and then rinsed out after an action period (1 to 10 minutes, or preferably 3 to 5 minutes) as needed.

Subsequently, the hair is towel-dried, if necessary, predampened, if necessary, with part of the hair keratin-reducing agent (component C), separated into individual strands, and rolled up in curlers. A quantity of the hair keratin-reducing agent (component C) sufficient for restructuring the hair, generally 50 g to 100 g (1.76 oz to 3.53 oz), or preferably (average length hair) 70 g to 90 g (2.47 oz to 3.17 oz), is then applied.

The oxidative hair colorant used in the process according to the present invention (component A) preferably contains, as a developer substance, one of the compounds selected from 1,4-diaminobenzene, 1,4-diamino-2-methylbenzene, 1,4-diamino-2,6-dimethylbenzene, 1,4-diamino-2,5-dimethylbenzene, 1,4-diamino-2,3-dimethylbenzene, 1,4-diamino-2-chlorobenzene, 4-di[(2-hydroxyethyl)amino]aniline, 4-[(2-methoxyethyl)amino]aniline, 1,4-diamino-2-(2-hydroxyethyl)benzene, 1,3-bis-[N(2-hydroxyethyl)-N-(4-aminophenyl)amino-2-propanol, and 2,'2-[1,2-ethanediyl-bis(oxy-2,1-ethandiyloxy)]bis-1,4-diaminobenzene.

The oxidative hair colorant used in the process of the present invention preferably contains, as a coupler substance, one of the compounds selected from 1,3-diaminobenzene, 2-amino-4-[(2-hydroxyethyl)amino]anisole, 2,4-diamino-1-fluoro-5-methylbenzene, 2,4-diamino-1-methoxy-5-methylbenzene, 2,4-diamino-1-ethoxy-5-methylbenzene, 2,4-diamino-1-(2-hydroxy-ethoxy)-5-methylbenzene, 2,4-di[(2-hydroxyethyl)amino]-1,5-dimethoxybenzene, 2,4-diamino-1-(2-hydroxy-ethoxy)benzene, 3-di[(2-hydroxyethyl)amino]aniline, 4-amino-1-ethoxy-2-di[(2-hydroxyethyl)amino]benzene, 3-[(2-hydroxy-ethyl)amino]aniline, 3-[(2-aminoethyl)amino]aniline, 1,3-di(2,4-diami-nophenoxy)propane, 2,4-dimethoxy-1,3-diaminobenzene, 2,6-bis(2-hydroxyeth-yl)aminotoluene, 3-dimethylaminophenol, 5-amino-2-methylphenol, 5-amino-4-fluoro-2-methylphenol, 5-amino-4-methoxy-2-methylphenol, 5-amino-4-ethoxy-2-methylphenol, 3-amino-2,4-dichlorophenol, 3-diethylaminophenol, 3-amino-2-chloro-6-methylphenol, 3-aminophenol, 3-[(amidomethyl)amino]phenol, 5-[(2-hydroxyethyl)amino]-2-methylphenol, 3-[(2-hydroxyethyl)amino]phenol, 5-amino-2-ethyl-phenol, 5-[(3-hydroxypropyl)amino]-2-methylphenol, 3-[(2,3-dihydroxypropyl)amino]-2-methyl-phenol, 3-[(2-hydroxyethyl)amino]-2-methylphenol, 5-amino-4-chloro-2-methylphenol, methylene-dioxyphenol, resorcinol, methylresorcinol, and 4-chlororesorcinol.

The coupler and developer substances are preferably contained in the oxidative hair colorant in a quantity of from 1 to 10% by weight.

The oxidative hair colorant (A) can also contain direct-penetrating dyes in a quantity of from 1 to 5 wt %.

Immediately before use of the ready-to-use oxidative hair colorant, it must be prepared by mixing the dye basis with an oxidative agent, typically a 3 to 12%, or preferably 6%, aqueous hydrogen peroxide solution or emulsion.

The intermediate treatment agent used in the present process preferably has a pH of from 2 to 3. It preferably contains an inorganic or organic acid selected from phosphoric acid, citric acid, glyoxylic acid, lactic acid, oxalic acid, acetic acid, and succinic acid. It is especially preferred if it also contains betaine.

Permanent restructuring agents (component C) that can be used in the process described herein are those that are based on typical hair keratin-reducing materials such as, for example, salts of sulfuric acid or certain mercapto compounds, particularly salts or esters of mercapto carboxylic acids. The restructuring component (C) contains the keratin-reducing compounds in the quantities typical for restructuring, for example, the ammonium salts of mercaptoacetic acid or thiolactic acid or cysteine, in a concentration of from 6 to 12 percent by weight. The pH value of the alkaline restructuring agents is generally 7 to 10, wherein the pH is preferably set with ammonia, monoethanolamine, ammonium carbonate, or ammonium hydrogen carbonate.

If the restructuring component (C) is adjusted to be acidic (for example to a pH=6.5 to 6.9), then esters of mercapto carboxylic acids are used such as, for example, monothioglycol acid glycol esters or -glycerin esters, with mercapto acetamides or 2-mercaptopropionic acid amides being preferred, in a concentration of from 2 to 14 percent by weight; or the salts of the sulfuric acid, for example, sodium, ammonium, or monoethanol ammonium sulfite, in a concentration of from 3 to 8 percent by weight (calculated as $SO_2$).

It is preferred that the hair keratin-reducing compound used be salt or the derivative of a mercapto carboxylic acid. It is especially preferred that the keratin-reducing compound be selected from mercaptoacetic acid, cysteine, and thiolactic acid, or salts thereof.

To increase the effect, bulking and penetration agents, for example, urea, polyvalent alcohols, ether, melamine, alkali or ammonium thiocyanate, isopropanol, imidazolidine-2-on, 2-pyrrolidone, and 1-methyl-2-pyrrolidone can be added to the restructuring component (C) in a concentration of about 0.5 to 50 percent by weight, or preferably 2 to 30 percent by weight.

It is advantageous if the permanent restructuring agent (C) also contains the disulfide of a hair keratin-reducing compound (thiol), particularly dithioglycolate. The preferred quantity for use is 2 to 20 wt %, or preferably 3 to 10 wt %, wherein the ratio between the hair keratin-reducing compound and the disulfide is preferably 2:1 to 1:2, or particularly 2:1 to 1:1.

After an action time has elapsed that is sufficient for the permanent restructuring, which is 1 to 30 minutes, or preferably 2 to 20 minutes, depending on hair quality, the pH value, and the restructuring effectiveness of the color-providing restructuring agent as well as on the application temperature, the hair is, if necessary, rinsed with water, and then fixed with an oxidative agent.

The fixing agent is used in a quantity of about 50 to 200 g (1.76 to 7.05 oz) depending on hair thickness. Any oxidizing agent that has been used before in fixing agents can be used for the fixation. Examples of such oxidizing agent are potassium bromate, sodium bromate, sodium perborate, dehydroascorbic acid, hydrogen peroxide, and urea peroxide. The concentration of the oxidizing agent varies depending on application time (normally 1 to 40 minutes, or preferably 5 to 20 minutes) and application temperature (25 to 50 degrees Celsius (77° F. to 122° F.)). Normally, oxidizing agents are used in a concentration of about 0.5 to 12.0% by weight in the aqueous fixing agents. The fixing agents can obviously contain other materials, for example, weak acids or peroxide stabilizers.

Both the color-providing restructuring agent used with the process according to the present invention and the fixing agent can be present in the form of an aqueous solution or an emulsion, as well as in a thickened form on an aqueous basis, particularly as a cream, gel, or paste.

It is especially preferred that the fixation be in low viscosity liquid form. In conjunction with the preferred direct application of the fixation without an intermediate rinsing, an optimum color result is achieved. It is preferred that the fixing agent be an oxidation agent-containing, liquid preparation with a viscosity of from 1 to 100 mPa·s at 25 degrees Celsius (77° F.), wherein viscosity of from 1 to 10 mPa·s at 25 degrees Celsius (77° F.) is especially preferred. The viscosity values are based on measurements with a Haake rotational viscometer, type VT 501, at a shear speed of 64.5 per second.

It is also possible to fill this agent into aerosol cans under pressure and to release it as aerosol foam.

Of course, the hair colorant, the restructuring agent, and the fixing agent can contain all the additives customary and known for these types of agents, for example, thickeners, such as kaolin, bentonite, fatty acids, higher fatty alcohols, starches, polyacryl acid, cellulose derivatives, alginates, Vaseline, or paraffin oil, wetting agents, or emulsifiers from the classes of the anionic, cationic, amphoteric, or nonionic surface-active substances, for example, fatty alcohol sulfates, fatty alcohol ether sulfates, alkylsulphonates, alkylbenzene sulfates, quaternary ammonium salts, alkyl betaine, oxyethylated fatty alcohols, oxyethylated alkyl phenols, fatty acid alkanolamides, or oxyethylated fatty acid esters, other opacifying agents such as polyethylene glycol esters, or alcohols such as ethanol, propanol, isopropanol, or glycerin, solubilizing agents, stabilizers, buffers, perfume oils, hair-conditioning agents, as well as hair-care components such as cationic polymers, lanolin derivatives, cholesterol, pantothenic acid, creatin, or betaine.

Furthermore, visual lighteners in the form of coumarin, stilbene, naphthalimide, benzoxazol, or styryl derivatives can be added to these agents. The components mentioned are used in standard quantities for such purposes; for example, the wetting agents and emulsifying agents can be contained in concentrations of about 0.2 to 30 weight %, while the thickeners can be contained in a quantity of about 0.1 to 25 weight %; and each case is based on the ready-to-use agent.

Suitable cationic polymers are preferably hair-conditioning polymers. Cationic polymers can be homo- or copolymers, where the quaternary nitrogen groups are contained either in the polymer chain or preferably as substituents on one or more of the monomers. The ammonium group-containing monomers can be copolymerized with non-cationic monomers. Suitable cationic monomers are unsaturated, radical polymerizable compounds carrying at least one cationic group, particularly ammonium-substituted vinyl monomers such as trialkyl methacryl oxyalkyl ammonium, trialkyl acryloxyalkyl ammonium, dialkyl diallyl ammonium, and quaternary vinyl ammonium monomers with groups containing cyclic, cationic nitrogen such as pyridinium, imidazolium, or quaternary, e.g. alkyl vinyl imidazolium, alkyl vinyl pyridinium, or alkyl vinyl pyrrolidone salts. The alkyl groups of these monomers are preferably lower alkyl groups, such as C1 to C7 alkyl groups, with C1 to C3 alkyl groups being especially preferred.

The ammonium group-containing monomers can be copolymerized with non-cationic monomers. Suitable comonomers are, for example, acrylamide, methacrylamide, alkyl- and dialkyl acrylamide, alkyl- and dialkyl methacrylamide, alkyl acrylate, alkyl methacrylate, vinyl caprolactone, vinyl caprolactam, vinyl pyrrolidone, vinyl ester, e.g. vinyl acetate, vinyl alcohol, propylene glycol, or ethylene glycol, wherein the alkyl groups of these monomers are preferably C1 to C7 alkyl groups, with C1 to C3 alkyl groups being especially preferred.

Suitable polymers with quaternary amine groups are, for example, polymers described in the CTFA Cosmetic Ingredient Dictionary under the designations Polyquaternium such as methyl vinyl imidazolium chloride/vinyl pyrrolidone copolymer (Polyquaternium-16) or quaternized vinyl pyrrolidone/dimethylaminoethyl methacrylate copolymer (Polyquaternium-11), or homo- and copolymers of dimethyl diallyl ammonium chloride (Polyquaternium-6 and -7), quaternized hydroxyethyl cellulose (Polyquaternium-10), or quaternized guar derivatives.

Of the cationic polymers that can be contained in the agent according to the present invention the following, for example, are suitable: vinyl pyrrolidone/dimethylamino ethylmethacrylate methosulfate copolymer, sold under the trade names Gafquat® 755 N and Gafquat® 734 by Gaf Co. in the USA; Gafquat® 734 is especially preferred. Other cationic polymers include, for example, a copolymer sold by BASF in Germany under the trade name LUVIQUAT® HM 550 consisting of polyvinyl pyrrolidone and imidazolimine methochloride; a terpolymer sold by Calgon in the USA under the trade name Merquat® Plus 3300 consisting of dimethyl diallyl ammonium chloride, sodium acrylate, and acrylamide; a terpolymer from ISP in the USA sold under the trade name Gaffix® VC 713 consisting of vinyl pyrrolidone, dimethylamino ethyl methacrylate, and vinyl caprolactam; and the copolymer sold by Gaf under the trade name Gafquat® HS 100 consisting of vinyl pyrrolidone/methacrylamidopropyltrimethyl ammonium chloride.

Suitable cationic polymers that are derived from natural polymers are cationic derivatives of polysaccharides, for example, cationic derivatives of cellulose, starch, or guar. Furthermore, chitosan and chitosan derivatives are suitable. Cationic polysaccharides have the general formula

$$G\text{-}O\text{---}B\text{---}N^+R^aR^bR^cX^-  \qquad (I)$$

G is an anhydroglucose residue, for example, starch or cellulose anhydroglucose;

B is a divalent bonding group, for example alkylene, oxyalkylene, polyoxyalkylene or hydroxy-alkylene;

$R^a$, $R^b$, and $R^c$, independently from one another, are alkyl, aryl, alkylaryl, arylalkyl, alkoxyalkyl, or alkoxyaryl each having 1 to 18 C atoms, wherein the total number of C atoms in $R^a$, $R^b$, and $R^c$ is preferably a maximum of 20;

$X^{(-)}$ is a common anion, preferably chloride, bromide, or sulfate.

A cationic cellulose is sold by Amerchol under the name Polymer JR and has the INCI designation Polyquaternium-10. An additional cationic cellulose has the INCI designation Polyquaternium-24 and is sold by Amerchol under the trade name Polymer LM-200. A suitable cationic guar derivative is sold under the trade name Jaguar® R and has the INCI designation Guar Hydroxypropyltrimonium Chloride.

Other suitable cationic polymers are chitosan, chitosan salts, and chitosan derivatives. The chitosans are completely or partially deacetylated chitins. To produce a chitosan, one preferably starts with the chitin contained in the shell residues of crustaceans, which, as a cheaper and natural raw material, is available in large quantities. The molecular weight of the chitosan can be distributed across a broad spectrum, for example, of from 20,000 to approx. 5 million g/mol (700 to about 176,000 oz/mol). For example, a suitable low-molecular-weight chitosan is one with a molecular weight of from 30,000 to 70,000 g/mol (1,100 to 25,000 oz/mol). Preferably, however, the molecular weight is greater than 100,000 g/mol (3,527 oz/mol), or especially preferred is a molecular weight of from 200,000 to 700,000 g/mol (7,054 to 24,692 oz/mol). The level of deacetylation is preferably from 10 to 99%, with 60 to 99% being especially preferred.

A suitable chitosan is sold, for example, by Kyowa Oil&Fat in Japan under the trade name Flonac®. It has a molecular weight of 300,000 to 700,000 g/mol (10,582 to 24,692 oz/mol) and is deacetylated to 70 to 80%. A preferred chitosan salt is chitosonium pyrrolidone carboxylate, which, for example, is sold under the name Kytamer PC by Amerchol in the USA. The chitosan contained therein has a molecular weight of approx. 200,000 to 300,000 g/mol (7,054 to 10,582 oz/mol) and is deacetylated to 70 to 85%. Quaternated, alkylated, or hydroxyalkylated derivatives, for example, hydroxyethyl or hydroxybutyl chitosans can be considered chitosan derivatives.

The chitosans or chitosan derivatives are preferably present in their neutralized or partially neutralized form. The level of neutralization for the chitosan or the chitosan derivative is preferably at least 50%, with 70 to 100% being especially preferred, based on the number of free base groups. In principle, all cosmetically compatible inorganic or organic acids can be used as neutralizers such as formic acid, malic acid, succinic acid, tartaric acid, citric acid, malonic acid, oxalic acid, and pyrrolidone carboxylic acid, of which the citric acid is preferred.

Other suitable cation-active hair-conditioning compounds that can be contained in the restructuring agents, hair colorants, and fixing agents used in the process according to the present invention are cationic modified protein derivatives or cationic modified protein hydrolysates and are, for example, known under the INCI designations Lauryldimonium Hydroxypropyl Hydrolyzed Wheat Protein, Lauryldimonium Hydroxypropyl Hydrolyzed Casein, Lauryldimonium Hydroxypropyl Hydrolyzed Collagen, Lauryldimonium Hydroxypropyl Hydrolyzed Keratin, Lauryldimonium Hydroxypropyl Hydrolyzed Silk, Lauryldimonium Hydroxypropyl Hydrolyzed Soy Protein, or Hydroxypropyltrimonium Hydrolyzed Wheat, Hydroxypropyltrimonium Hydrolyzed Casein, Hydroxypropyltrimonium Hydrolyzed Collagen, Hydroxypropyltrimonium Hydrolyzed Keratin, Hydroxypropyltrimonium Hydrolyzed Rice Bran Protein, Hydroxypropyltrimonium Hydrolyzed Silk, Hydroxypropyltrimonium Hydrolyzed Soy Protein, and Hydroxypropyltrimonium Hydrolyzed Vegetable Protein.

Suitable cationically derived protein hydrolysates are substance mixtures, which, for example, receive glycidyl trialkyl ammonium salts or 3-halo-2-hydroxypropyl trialkyl ammonium salts via the conversion of alkaline, acidic, or enzyme-hydrolyzed proteins. Proteins that are used as starting materials for the protein hydrolysates can be of plant or animal origin. Customary starting materials are, for example, keratin, collagen, elastin, soy protein, rice protein, milk protein, wheat protein, silk protein, or almond protein. The hydrolysis results in material mixtures with mole masses in the range of approx. 100 to approx. 50,000. Customary, mean mole masses are in the range of about 500 to about 1,000. It is advantageous if the cationically derived protein hydrolysates have one or two long C8 to C22 alkyl chains and two or one short C1 to C4 alkyl chain accordingly. Compounds containing one long alkyl chain are preferred.

It is advantageous if the agent also contains cation-active silicon compounds. These compounds are substituted with cationic groups or groups that can be made cationic. Suitable cation-active silicon compounds either have at least one amino group or at least one ammonium group. Suitable silicon polymers with amino groups are known under the INCI designation Amodimethicone. These polymers are polydimethylsiloxanes with aminoalkyl groups.

After an action period for the fixing agent of 3 to 15 minutes, or preferably 5 to 10 minutes, the curlers are removed, the fixing agent is rinsed from the hair with water, if necessary, and the hair is then treated with a known acidic rinse. It is advantageous if the hair is then subsequently shaped into a water wave.

Surprisingly, with the process according to the present invention, both the coloring and permanent wave processes, which are typically separated, were successfully carried out on the same day in one treatment process with optimum hair conditioning and the accustomed restructuring results. Furthermore, there is very little color loss; thus, improved durability of the color and an efficient treatment sequence for the customer are achieved when compared to the conventional methods.

The hair colored and permanently restructured in this manner has significantly longer durability with respect to the hair color and to the restructuring. The process according to the present invention has the advantage that a color and restructuring of the hair and an improvement in shine is obtained one right after the other on the same day. This enables a conditioning and simultaneously efficient hair treatment. An additional advantage is the longer durability of the color in comparison to the application of color and permanent wave treatment with a one week break between treatments.

EXAMPLES

Example 1

Natural hair is first colored with the oxidative hair colorant of component A. The component is left on for 20 min. The hair is then neutralized with an acidic intermediate treatment agent (component B). After an action period of 3 minutes, the damp hair is rolled onto curlers with a diameter of 8 millimeters (0.27 in), and the wave agent (component C) is applied and allowed to work for 20 minutes. The wave agent is then rinsed out with water, the hair is fixed with a fixing agent (component D) for 10 minutes, and it is then treated with an acidic agent.

| Oxidative hair colorant (component A) | |
|---|---|
| Component (1) | |
| 1.00 g (0.04 oz) | castor oil, oxyethylated with 35 mol ethylene oxide |
| 0.20 g (0.007 oz) | sodium sulfite |
| 8.10 g (0.29 oz) | ammonia, 25% aqueous solution |
| 0.10 g (0.004 oz) | 3-aminophenol |
| 0.04 g (0.0014 oz) | amino-4-[(2-hydroxyethyl)amino]anisole |
| 0.60 g (0.021 oz) | resorcinol |
| 0.40 g (0.014 oz) | p-toluene diamine sulfate |
| 0.03 g (0.0011 oz) | 2-amino-5-methylphenol |
| 0.50 g (0.018 oz) | 4-amino-3-methylphenol |
| 0.30 g (0.011 oz) | cationic cellulose polymer (Polyquaternium-10) |
| 2.00 g (0.071 oz) | ethanol |
| balance to 100 g (3.52 oz) | water |

-continued

| Oxidative hair colorant (component A) | |
|---|---|
| Component (2) | |
| 12.00 g (0.42 oz) | hydrogen peroxide, 50% |
| 0.10 g (0.0035 oz) | salicylic acid |
| 0.20 g (0.0071 oz) | disodium hydrogen phosphate |
| 0.15 g (0.0053 oz) | o-phosphoric acid |
| 1.00 g (0.035 oz) | castor oil, oxyethylated with 35 mol ethylene oxide |
| 0.10 g (0.0035 oz) | vinylpyrrolidone/styrene-mixed polymer |
| 0.10 g (0.0035 oz) | perfume oil |
| Balance to 100 g (3.53 oz) | water |

Before use, 40 g (1.41 oz) of the liquid color vehicle (component (1)) is mixed with 40 g (1.41 oz) of the hydrogen peroxide solution (component (2)). The pH value of the ready-to-use agent obtained is 9.8. 120 g (4.23 oz) of the ready-to-use agent is applied to gray, human hair and the mixture is left in for 20 minutes at room temperature.

| Intermediate treatment agent (component B) | |
|---|---|
| 2.0 g (0.071 oz) | mixture of cetyl and stearyl alcohols |
| 1.0 g (0.035 oz) | Vaseline |
| 1.0 g (0.035 oz) | citric acid |
| 0.5 g (0.018 oz) | perfume oil |
| Balance to 100 g (3.53 oz) | water |

| Permanent wave agent (component C) | |
|---|---|
| 12.0 g (0.42 oz) | ammonium thioglycolate, 70% aqueous solution |
| 5.0 g 0.18 oz) | dithioglycolate |
| 1.0 g (0.035 oz) | ammonia, 25% aqueous solution |
| 4.0 g 0.14 oz) | ammonium hydrogen carbonate |
| 1.0 g (0.035 oz) | castor oil, oxyethylated with 35 mol ethylene oxide |
| 1.0 g (0.035 oz) | polydimethyl diallyl ammonium chloride homopolymer |
| (CTFA: POLYQUATERNIUM-6) | |
| 0.5 g (0.018 oz) | perfume oil |
| Balance to 100 g (3.53 oz) | water |

The acidic intermediate treatment agent has a pH value of 3.2 and neutralizes the alkaline component A. Subsequently, the permanent wave solution is evenly distributed to the rolled hair. The solution is then left on the hair for 20 min, and a hood-type infrared radiator is used at a temperature of 40° C. (104° F.). The rolled up hair is then treated with 80 g (2.82 oz) of the following fixing agent.

| Liquid fixing agent (component D) | |
|---|---|
| 4.00 g (0.14 oz) | hydrogen peroxide, 50% |
| 0.10 g (0.0035 oz) | salicylic acid |
| 0.20 g (0.0071 oz) | disodium hydrogen phosphate |
| 0.15 g (0.53 oz) | o-phosphoric acid |
| 1.00 g (0.035 oz) | castor oil, oxyethylated with 35 mol ethylene oxide |

-continued

| Liquid fixing agent (component D) | |
|---|---|
| 0.10 g (0.0035 oz) | vinylpyrrolidone/styrene-mixed polymer |
| 0.10 g (0.0035 oz) | perfume oil |
| balance to 100 g (3.53 oz) | water |

There is then an action period of 10 minutes. After the action period has elapsed, the curlers are removed and the hair is thoroughly rinsed with warm water and then treated with a known acidic rinse. The hairstyle is then created in the normal manner with a blow dryer and brush.

The hair is colored to a warm brown tone and exhibits a beautiful shine.

Example 2

Hair damaged by oxidation is first colored with the oxidative hair colorant of component A. The component is left on for 20 min. The hair is then neutralized with an acidic intermediate treatment agent (component B). After an action period of 5 minutes, the damp hair is rolled onto curlers with a diameter of 10 millimeters (0.34 in), and the wave agent (component C) is applied and allowed to work for 10 minutes. The wave agent is then rinsed out with water, the hair is fixed, and it is then treated with an acidic material.

| Oxidation hair colorant (component A) | |
|---|---|
| Component (1) | Liquid color vehicle |
| 2.8 g (0.099 oz) | 2,5-diamino toluene sulfate |
| 1.0 g (0.035 oz) | resorcinol |
| 0.4 g (0.014 oz) | m-aminophenol |
| 0.2 g (0.0071 oz) | 2-amino-4-(2'-hydroxyethyl-amino)anisole sulfate |
| 5.0 g (0.18 oz) | lauryl glucoside (Plantaren 1200 sold by Henkel KGaA in Germany) |
| 5.0 g (0.18 oz) | sodium lauryl alcohol diglycol ether sulfate, 28% aqueous solution |
| 0.1 g (0.0035 oz) | valine |
| 0.3 g (0.011 oz) | ascorbic acid |
| 0.1 g (0.0035 oz) | ethylene diamine tetraacetic acid |
| 0.1 g (0.0035 oz) | keratin hydrolysate |
| 12.2 g (0.43 oz) | ammonia, 25% aqueous solution |
| 16.0 g (0.56 oz) | propylene glycol |
| balance to 100 g (3.53 oz) | water |

| Component (2): | Hydrogen peroxide - emulsion |
|---|---|
| 10.0 g (0.35 oz) | cetylstearyl alcohol |
| 3.0 g (0.11 oz) | acrylates/Ceteth-20 Itaconate Copolymer (Structure 3001 sold by the National Starch & Chemical Company in the USA) |
| 5.0 g (0.18 oz) | polyoxypropylene oxide(1)polyoxyethylenoxide(9) laurylether (PPG-1-PEG-9 lauryl ether) |
| 4.0 g (0.14 oz) | sodium lauryl alcohol diglycol ether sulfate, 28% aqueous solution |
| 20.0 g (0.71 oz) | hydrogen peroxide, 35% aqueous solution |
| 0.3 g (0.011 oz) | perfume |
| balance to 100 g (3.53 oz) | water |

Before use, 40 g (1.41 oz) of the liquid color vehicle is mixed with 80 g 2.82 g (oz) of the hydrogen peroxide-emulsion. The pH value of the ready-to-use agent obtained is 10. 120 g (4.23 oz) of the ready-to-use agent is applied to gray, human hair and the mixture is left in for 20 minutes at room temperature.

| Intermediate treatment agent (component B) | |
|---|---|
| 2.00 g (0.071 oz) | cetyltrimethylammonium chloride |
| 8.00 g (0.28 oz) | citric acid |
| 10.00 g (0.35 oz) | lactic acid, 90% |
| 5.00 g 0.18 oz) | glyoxylic acid |
| balance to 100 g (3.53 oz) | water |

| Permanent restructuring agent (component C) | |
|---|---|
| 5.0 g (0.18 oz) | ammonium thioglycolate, 70% aqueous solution |
| 0.6 g (0.021 oz) | ammonia, 25% aqueous solution |
| 3.0 g (0.11 oz) | ammonium hydrogen carbonate |
| 2.0 g (0.071 oz) | castor oil, oxyethylated with 35 mol ethylene oxide |
| 0.5 g (0.018 oz) | perfume oil |
| balance to 100 g (3.53 oz) | water |

The acidic intermediate treatment (component B) has a pH value of 3.0 and thus neutralizes the alkaline component A. After the action period of 5 minutes, the permanent wave solution (component C) is evenly distributed to the rolled up hair. The solution is then left on the hair for 10 minutes, and a hood-type infrared radiator is used at a temperature of 40° C. (104° F.). The rolled up hair is then treated with 80 g (2.82 oz) of the following fixing agent (component D).

| Viscous fixing agent (component D) | |
|---|---|
| 4.00 g 0.14 oz) | cetyl stearyl alcohol |
| 0.10 g (0.0035 oz) | vinylpyrrolidone/dimethylaminoethyl methacrylate methosulfate copolymer |
| 0.10 g (0.0035 oz) | salicylic acid |
| 0.30 g (0.011 oz) | perfume oil |
| balance to 100 g (3.53 oz) | water |

There is then an action period of 15 minutes. The curlers are subsequently removed, and the hair is thoroughly rinsed with warm water. The hairstyle is then created in the normal manner with a blow dryer and brush.

The hair has taken on an even, dark brown tone, exhibits a smooth, pleasant hold, and has a beautiful shine.

The invention claimed is:

1. A process for coloring and permanently restructuring hair, wherein
   (a) an oxidative hair colorant is applied to the hair based on at least one developer substance and at least one coupler substance,
   (b) the oxidative hair colorant is left on for 5 to 60 minutes,
   (c) the oxidative hair colorant is rinsed out of the hair,
   (d) an acidic intermediate treatment agent with a pH of from 2 to 6 is applied to the hair,
   (e) after an action period of from 1 to 10 minutes, the intermediate treatment agent is rinsed out, if necessary, and the hair is then rolled up onto curlers,
   (f) a keratin-reducing permanent restructuring agent in the form of a premixed aqueous solution is applied to the hair,
   (g) after an action period of from 1 to 30 minutes, the keratin-reducing agent is rinsed out, if necessary,
   (h) the hair is fixed with an oxidative material, and
   (i) after an action period of from 3 to 15 minutes, the hair is rinsed with water, if necessary, and then treated with an acidic rinse,
   wherein the permanent restructuring agent contains:
   a disulfide of a hair keratin-reducing compound and a hair keratin-reducing substance selected from the group consisting of mercaptoacetic acid, salts of mercaptoacetic acid, cysteine, salts of cysteine, thiolactic acid and salts of thiolactic acid; and
   wherein the keratin-reducing permanent restructuring agent is applied to the hair on the same day that the oxidative coloring agent is applied to the hair.

2. The process as recited in claim 1, wherein the developer substance is selected from 1,4-diaminobenzene, 1,4-diamino-2-methylbenzene, 1,4-diamino-2,6-dimethylbenzene, 1,4-diamino-2,5-dimethylbenzene, 1,4-diamino-2,3-dimethylbenzene, 1,4-diamino-2-chloro-benzene, 4-di[(2-hydroxyethyl)amino]aniline, 4-[(2-methoxyethyl)amino]aniline, 1,4-diamino-2-(2-hydroxyethyl)benzene, 1,3-bis-[N(2-hydroxyethyl)-N-(4-aminophenyl)amino-2-propanol, and 2,2'-[1,2-ethanediyl-bis(oxy-2,1-ethane-diyl)]bis-1,4-diaminobenzene.

3. The process as recited in claim 1, wherein the coupler substance is selected from 1,3-diaminobenzene, 2-amino-4-[(2-hydroxyethyl)-amino]anisole, 2,4-diamino-1-fluoro-5-methylbenzene, 2,4-diamino-1-methoxy-5-methylbenzene, 2,4-diamino-1-ethoxy-5-methylbenzene, 2,4-diamino-1-(2-hydroxyethoxy)-5-methylbenzene, 2,4-di[(2-hydroxyethyl)amino]-1,5-dimethoxy-benzene, 2,4-diamino-1-(2-hydroxyethoxy)benzene, 3-di[(2-hydroxyethyl)amino]-aniline, 4-amino-1-ethoxy-2-di[(2-hydroxyethyl)amino]benzene, 3-[(2-hydroxyethyl)amino]aniline, 3-[(2-aminoethyl)amino]aniline, 1,3-di(2,4-diaminophenoxy)-propane, 2,4-dimethoxy-1,3-diaminobenzene, 2,6-bis(2-hydroxyethyl)amino-toluene, 3-dimethylaminophenol, 5-amino-2-methylphenol, 5-amino-4-fluoro-2-methylphenol, 5-amino-4-methoxy-2-methylphenol, 5-amino-4-ethoxy-2-methylphenol, 3-amino-2,4-dichlorophenol, 3-diethylaminophenol, 3-amino-2-chloro-6-methylphenol, 3-aminophenol, 3-[(amidomethyl)amino]phenol, 5-[(2-hydroxyethyl)amino]-2-methylphenol, 3-[(2-hydroxyethyl)amino]phenol, 5-amino-2-ethylphenol, 5-[(3-hydroxypropyl)amino]-2-methylphenol, 3-[(2,3-dihydroxypropyl)amino]-2-methylphenol, 3-[(2-hydroxyethyl)-amino]-2-methyl-phenol, 5-amino-4-chloro-2-methylphenol, methylenedioxyphenol, resorcinol, methylresorcinol, and 4-chlororesorcinol.

4. The process as recited in claim 1, wherein the action period of the oxidative hair colorant is 10 to 45 minutes.

5. The process as recited in claim 1, wherein the intermediate treatment agent contains betaine, citric acid, lactic acid, and/or glyoxylic acid.

6. The process as recited in claim 1, wherein the intermediate treatment agent has a pH of from 2 to 3.

7. The process as recited in claim 1, wherein the intermediate treatment agent has an action period of from 3 to 5 minutes.

8. The process as recited in claim 1, wherein the hair keratin-reducing substance is present in the permanent restructuring agent in a quantity of from 2 to 15 percent by weight.

9. The process as recited in claim 1, wherein the disulfide of the hair keratin-reducing compound is dithioglycolate.

10. The process as recited in claim 1, wherein the disulfide of the hair keratin-reducing compound is contained in the permanent restructuring agent in a quantity of from 2 to 20 percent by weight.

11. The process as recited in claim 1, wherein the ratio of the hair keratin-reducing substance to the disulfide of the hair keratin-reducing compound is 2:1 to 1:1.

12. The process as recited in claim 1, wherein the hair is treated with the fixing agent, without rinsing the restructuring agent out of the hair prior to that.

13. The process as recited in claim 1, wherein an acidic prefixing agent is applied to the hair after the action period of the restructuring agent and before the treatment with the fixing agent.

* * * * *